US008394950B2

(12) United States Patent
Furneaux et al.

(10) Patent No.: US 8,394,950 B2
(45) Date of Patent: Mar. 12, 2013

(54) ANALOGUES OF COFORMYCIN AND THEIR USE FOR TREATING PROTOZOAN PARASITE INFECTIONS

(75) Inventors: Richard Hubert Furneaux, Wellington (NZ); Peter Charles Tyler, Wellington (NZ); Gary Brian Evans, Lower Hutt (NZ); Vern L. Schramm, New Rochelle, NY (US); Kami Kim, New York, NY (US); Richard Fröhlich, Wellington (NZ)

(73) Assignees: Industrial Research Limited, Lower Hutt (NZ); Albert Einstein College of Medicine of Yeshiva University, Bronx, NY (US)

( * ) Notice: Subject to any disclaimer, the term of this patent is extended or adjusted under 35 U.S.C. 154(b) by 644 days.

(21) Appl. No.: 12/223,746

(22) PCT Filed: Feb. 22, 2007

(86) PCT No.: PCT/NZ2007/000031
§ 371 (c)(1),
(2), (4) Date: Feb. 17, 2009

(87) PCT Pub. No.: WO2007/097643
PCT Pub. Date: Aug. 30, 2007

(65) Prior Publication Data
US 2009/0227532 A1 Sep. 10, 2009

Related U.S. Application Data

(60) Provisional application No. 60/775,963, filed on Feb. 22, 2006.

(51) Int. Cl.
*C07H 19/00* (2006.01)
*C07H 19/22* (2006.01)
*A01N 43/04* (2006.01)
*A61K 31/70* (2006.01)
(52) U.S. Cl. .................. 536/27.1; 536/27.11; 514/43
(58) Field of Classification Search .................. None
See application file for complete search history.

(56) References Cited

U.S. PATENT DOCUMENTS

| | | | |
|---|---|---|---|
| 5,985,848 A | 11/1999 | Furneaux et al. |
| 6,066,722 A | 5/2000 | Furneaux et al. |
| 6,228,847 B1 | 5/2001 | Furneaux et al. |
| 6,492,347 B2 | 12/2002 | Furneaux et al. |
| 6,693,193 B1 | 2/2004 | Furneaux et al. |
| 6,803,455 B2 | 10/2004 | Furneaux et al. |
| 7,022,852 B2 | 4/2006 | Furneaux et al. |
| 7,098,334 B2 | 8/2006 | Furneaux et al. |
| 7,109,331 B2 | 9/2006 | Furneaux et al. |
| 7,211,653 B2 | 5/2007 | Furneaux et al. |
| 7,211,677 B2 | 5/2007 | Furneaux et al. |
| 7,390,890 B2 | 6/2008 | Furneaux et al. |
| 7,405,297 B2 | 7/2008 | Furneaux et al. |
| 7,553,839 B2 | 6/2009 | Evans et al. |
| 7,655,795 B2 | 2/2010 | Evans et al. |
| 2006/0160765 A1 | 7/2006 | Evans et al. |
| 2006/0217551 A1 | 9/2006 | Evans et al. |
| 2007/0015772 A1 | 1/2007 | Furneaux et al. |
| 2008/0280334 A1 | 11/2008 | Lenz et al. |
| 2009/0233948 A1 | 9/2009 | Evans et al. |
| 2009/0239885 A1 | 9/2009 | Evans et al. |
| 2009/0325986 A1 | 12/2009 | Furneaux et al. |
| 2010/0062995 A1 | 3/2010 | Schramm |
| 2010/0094003 A1 | 4/2010 | Evans et al. |
| 2010/0168141 A1 | 7/2010 | Evans et al. |
| 2010/0222370 A1 | 9/2010 | Schramm et al. |
| 2011/0046167 A1 | 2/2011 | Clinch et al. |
| 2011/0086812 A1 | 4/2011 | Schramm |
| 2011/0092521 A1 | 4/2011 | Furneaux et al. |
| 2011/0130412 A1 | 6/2011 | Clinch et al. |

FOREIGN PATENT DOCUMENTS

| | | |
|---|---|---|
| WO | 2005033076 A1 | 4/2005 |
| WO | WO 2005/118532 | 12/2005 |
| WO | WO 2006/123953 | 11/2006 |
| WO | WO 2007/016291 | 2/2007 |
| WO | WO 2007/069923 | 6/2007 |
| WO | WO 2007/097647 | 8/2007 |
| WO | WO 2007 097648 | 8/2007 |
| WO | WO 2008 030118 | 3/2008 |
| WO | WO 2008/030119 | 3/2008 |
| WO | WO 2008/039324 | 4/2008 |
| WO | WO 2008/079028 | 7/2008 |
| WO | 2009082247 A1 | 7/2009 |
| WO | 2010033236 A2 | 2/2010 |
| WO | 2011008110 A1 | 1/2011 |

OTHER PUBLICATIONS

Banker, Modern Pharmaceutics, Third Edition, Marcel Dekker, Inc., published 1996, p. 596.*
Balant, 2003. Metabolic Considerations in Prodrug Design. Burger's Medicinal Chemistry, Drug Discovery and Development, pp. 975-977.*
Ting L-M et al., entitled "Targeting a novel *Plasmodium falciparum* purine recycling pathway with specific immucillins," J. Biol. Chem. 2005, vol. 280, No. 10, pp. 9547-9554. Epub Dec. 2, 2004.
Brown DM et al., entitled "L-nucleoside analogues as potential antimalarials that selectively target *Plasmodium falciparum* adenosine deaminase," Nucleosides and Nucleotides 1999, vol. 18, Nos. 11 &12, pp. 2521-2532 [Abstract Only]. "PCT Notification Concerning Transmittal of International Preliminary Report on Patentability" dated Sep. 4, 2008 issued by the International Bureau of WIPO in connection with PCT International Patent Applicaiton No. PCT/NZ2007/000031 , 6 pages.
Brown DM et al., entitled "L-nucleoside analogues as potential antimalarials that selectively target *Plasmodium falciparum* adenosine deaminase," Nucleosides and Nucleotides 1999, vol. 18, Nos. 11 &12, pp. 2521-2532.

* cited by examiner

*Primary Examiner* — Layla Bland
(74) *Attorney, Agent, or Firm* — Amster, Rothstein & Ebenstein LLP

(57) ABSTRACT

This invention relates to compounds that are analogues of coformycin, pharmaceutical compositions containing the compounds, and methods of using the compounds for treating protozoan parasite infections, especially malaria.

19 Claims, 1 Drawing Sheet

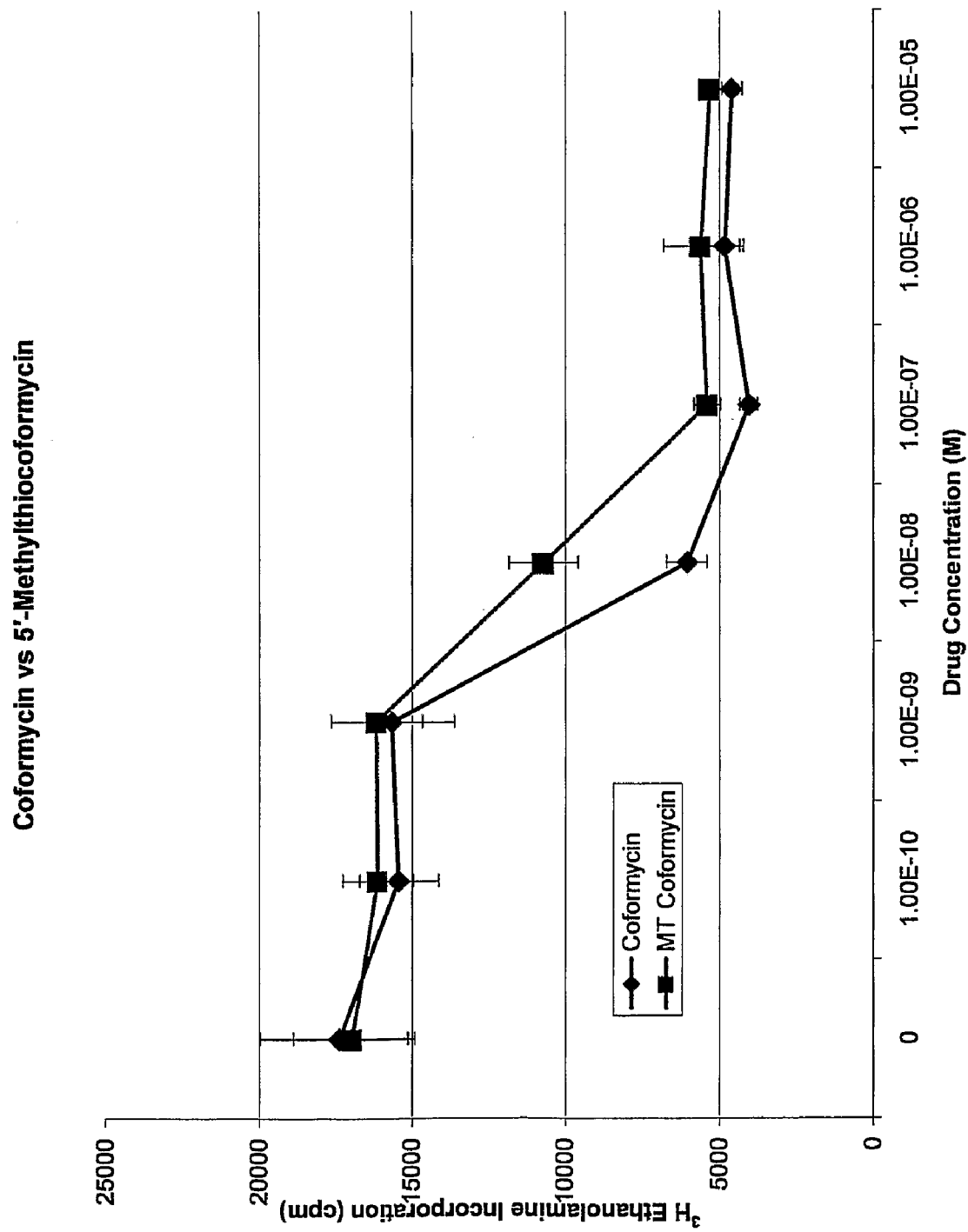

ANALOGUES OF COFORMYCIN AND THEIR USE FOR TREATING PROTOZOAN PARASITE INFECTIONS

CROSS-REFERENCE TO RELATED APPLICATIONS

This application is a national stage entry under 35 U.S.C. §371 of PCT International Patent Application No. PCT/NZ2007/000031, filed Feb. 22, 2007, and claims priority to U.S. Provisional Patent Application No. 60/775,963, filed Feb. 22, 2006, the contents of which are incorporated herein by reference in their entirety.

STATEMENT OF GOVERNMENT SUPPORT

This invention was made with government support under Grant No. AI049512awarded by the National Institutes of Health. The government has certain rights in the invention.

TECHNICAL FIELD

This invention relates to certain analogues of coformycin, the use of these compounds as pharmaceuticals, pharmaceutical compositions containing the compounds, and methods of treating protozoan parasite infections, especially malaria, using the compounds. The invention particularly relates to 5'-methylthiocoformycin.

BACKGROUND

Protozoan parasites cause some of the most devastating diseases world-wide. The parasites responsible for infectious diseases in man and animals, including fish, include those of the genera *Giardia, Trichomonas, Leishmania, Trypanosoma, Crithidia, Herpetomonas, Leptomonas, Histomonas, Eimeria, Isopora, Neospora* and *Plasmodium*.

*Plasmodium falciparum* is the organism that causes malaria in humans, and continues to be responsible for more than one million deaths per year. Drug resistance is increasing even to newer antimalarials such as mefloquine. This has led to an urgent need for new antimalarials both for chemotherapy and prophylaxis.

One feature common to protozoan parasites is that they do not have the ability to synthesise purines de novo and rely upon purine salvage and purine recycling to meet their purine needs. Purines are essential for the survival and replication of protozoan parasites, so they must obtain them from their mammalian hosts, which are able to synthesise purines by de novo pathways. The disruption of purine salvage pathways is therefore considered to be a means to specifically target protozoan parasite infections. Malaria is of particular interest, in that it causes the greatest economic and social harm.

Prior studies have shown that inhibitors of purine salvage enzymes kill malaria. Blocking *P. falciparum* purine nucleoside phosphorylase (PfPNP) with Immucillin-H, a transition state inhibitor based on inosine, induces starvation of purine leading to death of the organism. Because the transition state structures of both human and *P. falciparum* PNP enzymes are similar, transition state analogues based on inosine, such as Immucillin-H, inhibit both the human and *P. falciparum* PNPs.

*P. falciparum* is remarkable because of its small number of purine salvage enzymes despite the complete reliance on this pathway. The inventors have recently reported that the purine salvage enzymes *P. falciparum* adenosine deaminase (PfADA) and PfPNP each have two roles in the parasite and replace the functions in mammals of purine nucleoside phosphorylase (PNP), adenosine deaminase (ADA), methylthioadenosine phosphorylase (MTAP), adenosine phosphoribosyltransferase (APRT) and adenosine kinase (AK). The actions of PfADA and PfPNP permit the parasite to form hypoxanthine from erythrocyte purine pools and to recycle hypoxanthine from polyamine synthesis within the parasite. Hypoxanthine is a precursor for all purines and is a central metabolite for nucleic acid synthesis in *P. falciparum*.

5'-Methylthioadenosine is formed as a product of polyamine synthesis. In *P. falciparum*, it is recycled in a pathway in which PfADA converts it to 5'-methylthioinosine, then PfPNP converts 5'-methylthioinosine (and inosine) to hypoxanthine.

Following the observation that PfPNP uses 5'-methylthioinosine as a substrate, but human PNP (HsPNP) does not, the inventors recently synthesized transition state analogue inhibitors based on 5'-methylthioinosine (in particular 5'-methylthio-Immucillin-H) and reported them to be the first potent inhibitors that are selective for PfPNP relative to HsPNP. 5'-Methylthio-Immucillin-H showed 112-fold specificity for PfPNP. Further, 5'-methylthio-Immucillin-H was shown to kill *P. falciparum* in culture (see *J. Biol. Chem.*, 2005, 278, 9547-9554 and references therein).

The inhibition of PfADA has also been investigated. Coformycin, 2'-deoxycoformycin and the L-ribosyl analogues of the coformycins are known to be tight-binding inhibitors of both mammalian and *P. falciparum* ADAs [Daddona, P. E., Wiesmann, W. P., Lambros, C., Kelley, W. N., and Webster, H. K. (1984) *J Biol Chem* 259, 1472-1475; Wilson, D. K., Rudolph, F. B., and Quiocho, F. A (1991) *Science* 252, 1278-1284]. Coformycin and 2'-deoxycoformycin have comparable activity against bovine ADA and PfADA (J. Biol. Chem., 2005, 278, 9547-9554). A single dose of 2'-deoxycoformycin dramatically reduced parasitemia in primates with *Plasmodium knowlesi* [Webster, H. K., Wiesmann, W. P., and Pavia, C. S. (1984) *Adv. Exp. Med. Biol.*, 165 Pt A, 225-229], but 2'-deoxycoformycin is highly toxic in mammals. The challenge then was to discover a potent selective inhibitor of PfADA.

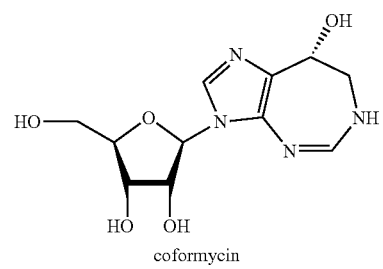

coformycin

Coformycin can be prepared by various methods. See for example: Thomas, H. Jeanette; Riordan, James M.; Montgomery, John A, *Nucleosides & Nucleotides* 1986, 5(4), 431-9; Hawkins, L. D.; Hanvey, J. C.; Boyd, F. L., Jr.; Baker, David C.; Showalter, H. D. Hollis, *Nucleosides Nucleotides* 1983, 2(5), 479-94; Ohno, Masaji; Yagisawa, Naomasa; Shibahara, Seiji; Kondo, Shinichi; Maeda, Kenji; Umezawa, Hamao, J. Am. Chem. Soc. 1974, 96(13), 4326-7; Shimazaki, Masami; Kondo, Shinichi; Maeda, Kenji; Ohno, Masaji; Umezawa, Hamao, J. Antibiotics, 1979 32, 537-538; Yamazaki, Masakuni; Harada, Takashi; Shibuya, Kyoichi; Hayashi, Emiko; Saito, Seiichi; Shimada, Nobuyoshi, Jpn. Kokai Tokkyo Koho (1988), JP 63226296 A2 19880920 CAN 110:

73872; Fr. Demande (1978), FR 2383966 19781013 CAN 91:57420; Umezawa, Hamao; Maeda, Kenji; Kondo, Shinichi. Ger. Offen. (1975), DE 2453649 CAN 83:59226; Umezawa, Hamao; Niida, Taro; Niwa, Tomizo; Tsuruoka, Takashi; Ezaki, Norio; Shomura, Takashi. Jpn. Tokkyo Koho (1970), JP 45012278 CAN 73:65025.

It has now been surprisingly found that certain analogues of coformycin are active against PfADA and are therefore potential therapeutic agents for the treatment or prevention of protozoan parasite infections including malaria.

It is therefore an object of the present invention to provide novel coformycin analogues for use against protozoan parasite-infections, especially malaria, or to at least provide a useful choice.

Statements of Invention

In a first aspect the invention provides a compound of formula (I):

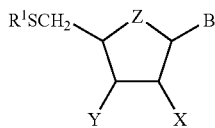

(I)

where $R^1$ is selected from an alkyl, aralkyl and aryl group each of which may be optionally substituted by one or more halogen atoms or one or more hydroxyl, amino, or carboxylic acid groups;

X is selected from hydrogen, hydroxyl and halogen;

Y is selected from hydrogen and hydroxyl;

Z is an oxygen atom or a methylene group;

B is the radical of formula (II):

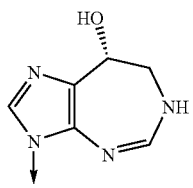

(II)

or a pharmaceutically acceptable salt thereof, or a prodrug thereof.

It is preferred that the compound of formula (I) is a compound of formula (IA):

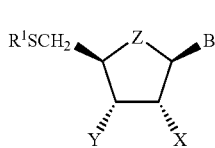

(IA)

where $R^1$, X, Y, Z, and B are as defined above.

Alternatively, it is preferred that the compound of formula (I) is a compound of formula (IB):

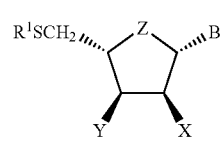

(IB)

where $R^1$, X, Y, Z, and B are as defined above.

Preferably $R^1$ is an alkyl group. In a preferred embodiment, $R^1$ is methyl.

X and Y are both preferably hydroxyl. Alternatively, X may be hydroxyl and Y may be hydrogen, or X may be hydrogen and Y may be hydroxyl.

Z is preferably an oxygen atom

Preferred compounds of the invention are:

(i) 5'-methylthiocoformycin [(8R)-8-hydroxy-3-(5-methylthio-β-D-ribofuranosyl)-3,6,7,8-tetrahydroimidazo[4,5-d][1,3]diazepine];

(ii) 2'-deoxy-5'-methylthiocoformycin [(8R)-8-hydroxy-3-(2-deoxy-5-methylthio-β-D-erythro-pentofuranosyl)-3,6,7,8-tetrahydroimidazo[4,5-d][1,3]diazepine];

(iii) 3'-deoxy-5'-methylthiocoformycin [(8R)-8-hydroxy-3-(3-deoxy-5-methylthio-β-D-ribofuranosyl)-3,6,7,8-tetrahydroimidazo[4,5-d][1,3]diazepine];

(iv) 2'-deoxy-5'-propylthiocoformycin [[(8R)-8-hydroxy-3-(5-propylthio-β-D-erythro-pentofuranosyl)-3,6,7,8-tetrahydroimidazo[4,5-d][1,3]diazepine]; and (v) 2'-deoxy-5'-phenylthiocoformycin [[(8R)-8-hydroxy-3-(5-phenylthio-β-D-erythro-pentofuranosyl)-3,6,7,8-tetrahydroimidazo[4,5-d][1,3]diazepine].

An especially preferred compound of the invention is 5'-methylthiocoformycin [(8R)-8-hydroxy-3-(5-methylthio-β-D-ribofuranosyl)-3,6,7,8-tetrahydroimidazo[4,5-d][1,3]diazepine].

In a second aspect of the invention there is provided a pharmaceutical composition comprising a pharmaceutically effective amount of a compound of the formula (I).

Preferably the pharmaceutical composition comprises:

(i) 5'-methylthiocoformycin [(8R)-8-hydroxy-3-(5-methylthio-β-D-ribofuranosyl)-3,6,7,8-tetrahydroimidazo[4,5-d][1,3]diazepine];

(ii) 2'-deoxy-5'-methylthiocoformycin [(8R)-8-hydroxy-3-(2-deoxy-5-methylthio-β-D-erythro-pentofuranosyl)-3,6,7,8-tetrahydroimidazo[4,5-d][1,3]diazepine];

(iii) 3'-deoxy-5'-methylthiocoformycin [(8R)-8-hydroxy-3-(3-deoxy-5-methylthio-β-D-ribofuranosyl)-3,6,7,8-tetrahydroimidazo[4,5-d][1,3]diazepine];

(iv) 2'-deoxy-5'-propylthiocoformycin [[(8R)-8-hydroxy-3-(5-propylthio-β-D-erythro-pentofuranosyl)-3,6,7,8-tetrahydroimidazo[4,5-d][1,3]diazepine]; or (v) 2'-deoxy-5'-phenylthiocoformycin [[(8R)-8-hydroxy-3-(5-phenylthio-β-D-erythro-pentofuranosyl)-3,6,7,8-tetrahydroimidazo[4,5-d][1,3]diazepine].

Most preferably the pharmaceutical composition comprises 5'-methylthiocoformycin [(8R)-8-hydroxy-3-(5-methylthio->D-ribofuranosyl)-3,6,7,8-tetrahydroimidazo[4,5-d][1,3]diazepine].

In another aspect of the invention there is provided a method of treating or preventing a protozoan parasite infection, especially malaria, comprising administering a pharmaceutically effective amount of a compound of formula (I) to a patient requiring treatment. The infection may be caused by any protozoan parasite including those of the genera Giardia, Trichomonas, Leishmania, Trypanosoma, Crithidia, Herpetomonas, Leptomonas, Histomonas, Eimeria, Isopora, Neospora, and Plasmodium. In a preferred embodiment the infection is malaria.

In another aspect the invention provides the use of a compound of formula (I) for the manufacture of a medicament for treating a protozoan parasite infection, especially malaria.

BRIEF DESCRIPTION OF DRAWING

FIG. 1 is a graph showing the ability of coformycin and 5'-methylthiocoformycin to prevent the growth of P. falciparum.

DETAILED DESCRIPTION

Definitions

The term "alkyl" is intended to include both straight- and branched-chain and cyclic alkyl groups and includes alkyl groups with an aza-, thia-, or oxa-substitution for one of the carbon atoms. The same terminology applies to the non-aromatic moiety of an aralkyl radical. Examples of straight- and branched-chain alkyl groups include: methyl, ethyl, n-propyl, iso propyl, n-butyl, iso-butyl, sec-butyl, t-butyl, n-pentyl, 1,1-dimethylpropyl, 1,2-dimethylpropyl, 2,2-dimethylpropyl, 1-ethylpropyl, 2-ethylpropyl, n-hexyl and 1-methyl-2-ethylpropyl. Examples of alkyl groups with an aza-, thia-, or oxa-substitution include 2-ethoxyethyl, 2-ethylthioethyl, 2-ethylaminoethyl. Examples of cyclic alkyl groups include: cyclopropyl, cyclobutyl, cyclopentyl, cyclohexyl and cycloheptyl. Examples of cyclic alkyl groups with an aza-, thia-, or oxa-substitution include 4-tetrahydropyran-4-yl, thiatetrahydropyran-1-yl and piperidin-4-yl.

The term "aryl" means an aromatic radical having 6 to 18 carbon atoms and includes heteroaromatic radicals. Examples include monocyclic groups, as well as fused groups such as bicyclic groups and tricyclic groups. Some examples include phenyl, indenyl, 1-naphthyl, 2-naphthyl, azulenyl, heptalenyl, biphenyl, indacenyl, acenaphthyl, fluorenyl, phenalenyl, phenanthrenyl, anthracenyl, cyclopentacyclooctenyl, and benzocyclooctenyl, pyridyl, pyrrolyl, pyridazinyl, pyrimidinyl, pyrazinyl, triazolyl, tetrazolyl, benzotriazolyl, pyrazolyl, imidazolyl, benzimidazolyl, indolyl, isoindolyl, indolizinyl, purinyl, indazolyl, furyl, pyranyl, benzofuryl, isobenzofuryl, thienyl, thiazolyl, isothiazolyl, benzothiazolyl, oxazolyl, and isoxazolyl.

The term "halogen" includes fluorine, chlorine, bromine and iodine.

The term "prodrug" as used herein means a pharmacologically acceptable derivative of the compound of formula (I) or formula (II), such that an in vivo biotransformation of the derivative gives the compound as defined in formula (I) or formula (II). Prodrugs of compounds of formula (I) or formula (II) may be prepared by modifying functional groups present in the compounds in such a way that the modifications are cleaved in vivo to give the parent compound.

The term "pharmaceutically acceptable salts" is intended to apply to non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

As used herein, the term "protecting group" means a group that selectively protects an organic functional group, temporarily masking the chemistry of that functional group and allowing other sites in the molecule to be manipulated without affecting the functional group. Suitable protecting groups are known to those skilled in the art and are described, for example, in Protective Groups in Organic Synthesis (3$^{rd}$ Ed.), T. W. Greene and P. G. M. Wuts, John Wiley & Sons Inc (1999).

As used herein, the term "protected hydroxyl group" means an hydroxyl group bound to a protecting group.

As used herein, the term "leaving group" means an atom (or a group of atoms) that is displaced as a stable species taking with it the bonding electrons when activated by a promoter. Suitable leaving groups and promoters are known to those skilled in the art and leaving groups commonly used at the anomeric centre of glycosyl donors and the associated promoters used to activate these leaving groups are described, for example, in "Synthesis and reactions of glycosides", P. J. Garegg, Advances in Carbohydrate Chemistry and Biochemistry, Vol. 59, 2004, Academic Press.

Mode of Action

In purine auxotrophs, including P. falciparum, purine salvage is essential. It is generally assumed that purine auxotrophs have parallel metabolic pathways for nucleoside and base salvage, thus making purine salvage difficult to target. However, there are no parallel pathways in P. falciparum. Instead, it has a single pathway with dual function.

The purine pathways of P. falciparum are:
adenosine is converted to inosine by PfADA;
hypoxanthine is liberated from inosine by PfPNP;
5'-methylthioadenosine (MTA) from the polyamine pathway is converted to 5'-methylthioinosine by PfADA;
hypoxanthine is liberated from 5'-methylthioinosine by PfPNP and the hypoxanthine is converted to inosine monophosphate (IMP) by a phosphoribosyltransferase; and
IMP is converted to nucleic acids by other enzymes.

PfADA and PfPNP are able to function on 5'-methylthio-substrates, unlike their human counterparts, which permits the pathway to function in adenosine, MTA and inosine recycling. This dual-function pathway explains why P. falciparum has no adenosine kinase or adenine PRT (enzymes found in other parasites to salvage adenosine and adenine). This renders P. falciparum, and any other protozoan parasites that are found to have similar dual function PNP and ADA enzymes, particularly sensitive to PNP and ADA inhibitors.

Simultaneous inhibition of host and parasite PNP of P. falciparum-infected erythrocytes with Immucillin-H induces purine-less death within 24 hours. Addition of hypoxanthine bypasses the PNP block and provides complete protection against Immucillin-H, establishing the target block at PNP. 5'-Methylthio-Immucillin-H was designed as an analogue of the transition state of the cleavage of 5'-methylthioinosine by PfPNP. It was found to have a 112-fold specificity for PfPNP over HsPNP, yet is able to kill P. falciparum growing in human erythrocytes.

The purine salvage pathway delineated above also suggests that inhibition of PfADA would interrupt purine salvage. PfADA appears to differ from the human enzyme by accepting adenosine and 5'-methylthioadenosine as substrates.

The compounds of the invention are inhibitors of the ADA of P. falciparum, with only weak activity against mammalian ADAs. They have been designed as analogues of the transition state for the ADA-catalyzed conversion of MTA to methylthioinosine. Thus, 5'-methylthiocoformycin is a pM inhibitor of PfADA, and shows >20,000 fold specificity for PfADA relative to HsADA. Importantly and unpredictably, because it cannot inhibit host ADA, it kills *P. falciparum* growing in human erythrocytes.

Although the compounds of the invention are expected to be particularly effective against *P. falciparum* and other protozoan parasites that are found to have similar dual function ADA enzymes, they will also compromise the viability and ineffectiveness of other protozoan parasites by restricting or blocking purine salvage, without damaging the mammalian host (whether that be human or animal, including fish) and are anticipated to be useful in treating protozoan parasite infections generally.

Enzyme Inhibition Studies

ADA action on adenosine or MTA was measured by the absorbance change at 265 nm. Inhibition studies measured both initial and slow-onset rates to establish both the initial dissociation constant ($K_i$) and the steady-state dissociation constant ($K_i^*$) as previously described [Kicska, G. A., Tyler, P. C., Evans, G. B., Furneaux, R. H., Kim, K., and Schramm, V. L. (2002) *J Biol Chem* 277, 3219-3225.]. $K_d$ is the lower of these values.

The enzyme inhibition results are shown in Example 5. 5'-Methylthiocoformycin is a potent, slow onset, tight binding inhibitor of PfADA and has little effect on mammalian ADAs. Coformycin is about 5 times more potent, but is not selective for PfADA, inhibiting mammalian ADAs with equivalent potency. Both coformycin and 2'-deoxycoformycin exhibit slow onset inhibition of all three enzymes with the tightest dissociation constants ranging from 27 to 110 pM. None of the 5'-functionalized analogues inhibited the bovine or human enzymes, whereas they all inhibited PfADA. The 5'-methylthio analogues were the most effective inhibitors of PfADA, with slow onset inhibition and high picomolar dissociation constants. The propyl- and phenylthio analogues also inhibited PfADA, but with no detectible slow onset. These compounds gave dissociation constants of 12 and 61 nM, respectively.

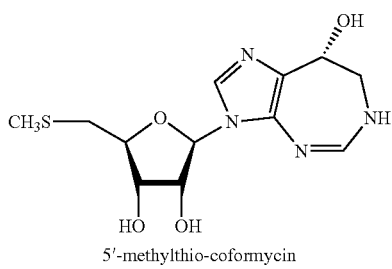

5'-methylthio-coformycin

Methods of Preparation

The compounds of the invention can be prepared either by modification of coformycin (or one of its known analogues) or by total synthesis.

Total synthesis involves the synthesis and use of a protected derivative of a compound of formula (II) for N-glycosylation of a protected base moiety of formula (III). Compounds of formula (III) can be prepared from commercially available sugars such as D-ribose and 2-deoxy-D-ribose by conventional carbohydrate synthetic methodology. Compounds of formula (II) can be prepared by methods such as those published in T. V. Truong and H. Rapoport *J. Org. Chem.* 1993, 58, 6090-6096.

A suitable approach to the modification of coformycin or its analogues, especially 2'-deoxy-, 2'-deoxy-2'-chloro- and 3'-deoxy-coformycin, involves creating a derivative of coformycin (or an analogue of coformycin) with the hydroxy and NH group of the base moiety protected, and the primary hydroxyl group of the sugar moiety selectively sulfonylated, displacing this sulfonate group with a metal thiolate and removing any remaining protecting groups from the base moiety.

The compounds of formula (I) and (V) may be prepared by any suitable method. Some examples of general methods are provided below in Methods A, B and C.

Method A: Compounds of formula (I) may be prepared by a process involving the following steps:

step (i) reacting a glycosyl donor compound of formula (III):

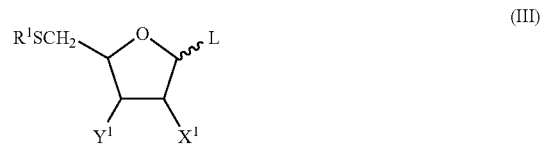

where
  L is a leaving group;
  $X^1$ is selected from hydrogen, halogen, acyloxy, and arylcarbonyloxy; and $Y^1$ is selected from hydrogen and acyloxy; or
  $X^1$ and $Y^1$ are oxygen atoms linked together by a protecting group; and
  $R^1$ is selected from an alkyl, aralkyl and aryl group each of which may be optionally substituted by one or more halogen atoms or one or more hydroxyl, amino, or carboxylic acid groups;
with a compound of formula (IV) in the presence of a glycosyl donor activating reagent:

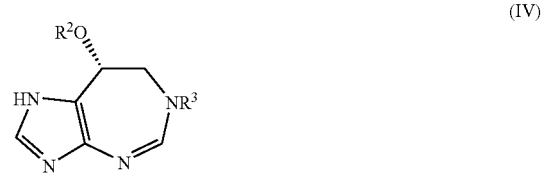

where
  $R^2$ is a protecting group; and
  $R^3$ is a protecting group;
step (ii) removal of the protecting groups to give hydroxyl or amine groups by any one or more of:
  (a) acid- and/or base-catalyzed hydrolysis;
  (b) acid- and/or base-catalyzed alcoholysis; and
  (c) catalytic hydrogenolysis.

L may be a halogen atom, or may be selected from alkylthio, arylthio, and trichloroacetimido. Preferred examples of the alkylthio group are methylthio and ethylthio. Preferred examples of the arylthio group are phenylthio and 4-methylphenylthio. When L is a halogen, the glycosyl donor activating reagent is preferably a mercury(II) salt or a silver(I) salt, such as $HgCl_2$ or AgOTf. When L is an alkyl or arylthio group, the glycosyl donor activating reagent is a thiophilic reagent, such as mercury(II) salt, or an activator, such as methyl triflate or N-iodosuccinimide. When L is trichloroacetimido, the glycosyl donor activating reagent is preferably trimethylsilyl triflate or boron trifluoride diethyl etherate.

When $X^1$ and $Y^1$ are oxygen atoms linked together by a protecting group, the protecting group is preferably isopropylidene or benzylidene. The acyloxy group of $X^1$ or $Y^1$ is preferably acetyloxy, benzoyloxy, propionyloxy or pivaloyloxy.

$R^2$ is preferably a silyl protecting group, for example tert-butyldimethylsilyl. $R^3$ is preferably an acyl or acyloxycarbonyl protecting group, such as a tert-butoxycarbonyl group.

Method B: Compounds of formula (I) may be prepared by a process involving the following steps:

step (i) selective sulfonylation of the primary hydroxyl group of a compound of formula (V):

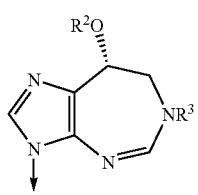

(V)

where
  X is selected from hydrogen, hydroxyl and halogen;
  Y is selected from hydrogen and hydroxyl;
  Z is an oxygen atom or a methylene group; and
  B is the radical of formula (VI)

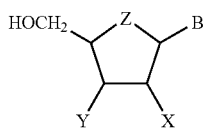

(VI)

where
  $R^2$ is a protecting group; and
  $R^3$ is a protecting group;

step (ii) reacting the product with a thiolate salt of formula $R^1SM$, where M is a metal cation and $R^1$ is as defined above in Method A; and step (iii) removing any remaining protecting groups.

$R^2$ is preferably a silyl protecting group, for example tert-butyldimethylsilyl. $R^3$ is preferably an acyl or acyloxycarbonyl protecting group such as a tert-butoxycarbonyl group. Preferably the sulfonylation agent is 2,4,6-triisopropylbenzenesulfonyl chloride or p-toluenesulfonyl chloride. It is also preferred that the metal cation is lithium, sodium, or potassium.

Removal of the protecting groups to give hydroxyl or amine groups can be effected prior to treatment with a thiolate salt in some cases and may typically be effected by any one or more of:
  (a) tetrabutylammonium fluoride;
  (b) ammonium fluoride;
  (c) acid- and/or base-catalyzed hydrolysis;
  (d) acid- and/or base-catalyzed alcoholysis; and
  (e) catalytic hydrogenolysis.

Method C: Compounds of formula (V) may be prepared by a process involving the following steps:

step (i) reacting a glycosyl donor compound of formula (III):

(III)

where
  L is a leaving group;
  $X^1$ is selected from hydrogen, halogen, acyloxy, and arylcarbonyloxy; and $Y^1$ is selected from hydrogen and acyloxy; or
  $X^1$ and $Y^1$ are oxygen atoms linked together by a protecting group; and
  $Y^2$ is acyloxy;
with a compound of formula (IV) in the presence of a glycosyl donor activating reagent or a metal hydride such as sodium hydride

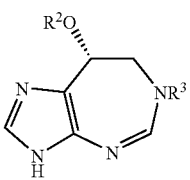

(IV)

where
  $R^2$ is a protecting group; and
  $R^3$ is a protecting group;

step (ii) removal of the protecting groups on the sugar moiety to give hydroxyl groups by any one or more of:
  (a) acid- and/or base-catalyzed hydrolysis;
  (b) acid- and/or base-catalyzed alcoholysis; and
  (c) catalytic hydrogenolysis.

General Aspects

The active compounds may be administered to a patient by a variety of routes, including orally, parenterally, by inhalation spray, topically, rectally, nasally, buccally or via an implanted reservoir. The amount of compound to be administered will vary widely according to the nature of the patient and the nature and extent of the disorder to be treated. Typically the dosage for an adult human will be in the range less than 1 to 1000 milligrams, preferably 0.1 to 100 milligrams. The specific dosage required for any particular patient will depend upon a variety of factors, including the patient's age, body weight, general health, sex, etc.

For oral administration the compounds can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried cornstarch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant.

The compounds may also be administered topically. Carriers for topical administration of the compounds of include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

EXAMPLES

The following examples further illustrate the invention. It is to be appreciated that the invention is not limited to the examples.
General All reagents were used as supplied; anhydrous solvents were obtained commercially. Air sensitive reactions were carried out under argon unless otherwise stated. Organic solutions were dried over $MgSO_4$ and the solvents were evaporated under reduced pressure. Chromatography solvents were distilled prior to use. Thin layer chromatography (t.l.c.) was performed on glass or aluminium sheets coated with 60 $F_{254}$ silica. Organic compounds were visualised under uv light or by use of a spray or dip of cerium(IV) sulfate (0.2%, w/v) and ammonium molybdate (5%) in sulfuric acid (2M), one of $I_2$ (0.2%) and KI (7%) in $H_2SO_4$ (M) or, for nitrogen-containing compounds, p-(N,N-dimethylamino)benzaldehyde (1%) in HCl (37%)-MeOH, 1:3 (100 ml) (Erlich reagent). Flash column chromatography was performed on Sorbsil C60 40/60 silica, Scharlau or Merck silica gel 60 (40-60 μm). Melting points were recorded on a Reichert hot stage microscope and are uncorrected. Optical rotations were recorded on a Perkin-Elmer 241 polarimeter with a path length of 1 dm and are in units of $10^{-1}$ deg $cm^2$ $g^{-1}$; concentrations are in g/100 ml.

NMR spectra were recorded on a BrukerAC300E spectrometer. $^1H$ spectra at 300 MHz were measured in $CDCl_3$, $CD_3OD$ or $CD_3CN$ (internal reference $Me_4Si$, δ 0), and $^{13}C$ spectra at 75.5 or 100.6 MHz in $CDCl_3$ (reference, solvent centre line, δ 77.0), $CD_3OD$ (reference, solvent centre line δ 49.0) or $CD_3CN$ (reference, solvent centre line δ 118.7, CN). Assignments of $^1H$ and $^{13}C$ resonances were based on 2D ($^1H$-$^1H$ DQF-COSY, $^1H$-$^{13}C$ HSQC) spectra, and DEPT experiments gave unambiguous data on the numbers of protons bonded to each carbon atom. The assignments of the $^{13}C$ resonances were consistent with the multiplicities observed. Coupling constants (J) are quoted in Hz. Infrared spectra were recorded on a Perkin-Elmer 1750 IR Fourier Transform using thin films on NaCl plates (thin film). Only characteristic absorptions are quoted. High resolution mass spectra (HRMS), ES data were collected on a Waters 2790-Micromass LCT mass spectrometer operated at a resolution of 5000 full width half height. Positive ion electrospray ionisation (ES+) spectra were calibrated relative to PEG with tetraoctylammonium bromide as the internal lock mass. Negative ion ES spectra were calibrated relative to poly-DL-alanine with Leu-enkephalin as the internal lock mass. Positive ion fast atom bombardment (FAB+) HRMS were measured on a VG 7070 instrument in a glycerol matrix, and positive ion electron impact (EI+) HRMS were measured on a VG 70SE instrument. Microanalyses were carried out by the Campbell Microanalytical Laboratory, University of Otago.

Human adenosine deaminase from human erythrocytes, bovine adenosine deaminase from bovine spleen, adenosine, potassium phosphate, and EDTA were purchased from Sigma-Aldrich Chemical Company. Malarial adenosine deaminase was obtained from Kami Kim (L.-M. Ting, W. Shi, A. Lewandowicz, V. Singh, A. Mwakingwe, M. R. Birck, E. A. Taylor Ringia, G. Bench, D. C. Madrid, P. C. Tyler, G. B. Evans, R. H. Furneaux, V. L. Schramm, K Kim *J. Biol. Chem.*, 2005, 280, 9547-9554). Bovine adenosine deaminase was obtained as an ammonium sulfate precipitate and was therefore buffer exchanged into 20 mM potassium phosphate buffer, pH 7.0 prior to use in enzyme assays. Concentrations of inhibitors were determined spectrophotometrically using the extinction coefficient of 8250 $M^{-1}cm^{-1}$ at 282 nm.

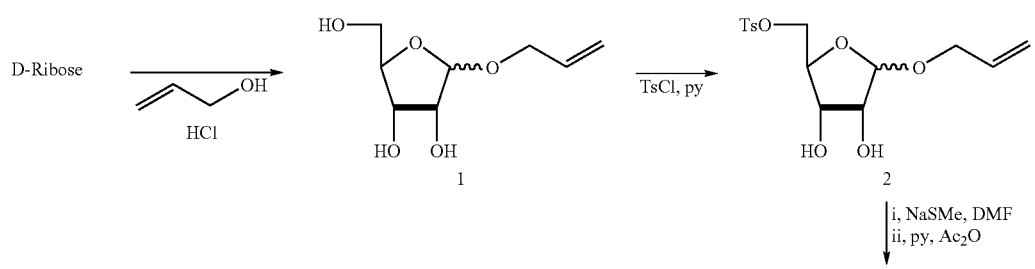

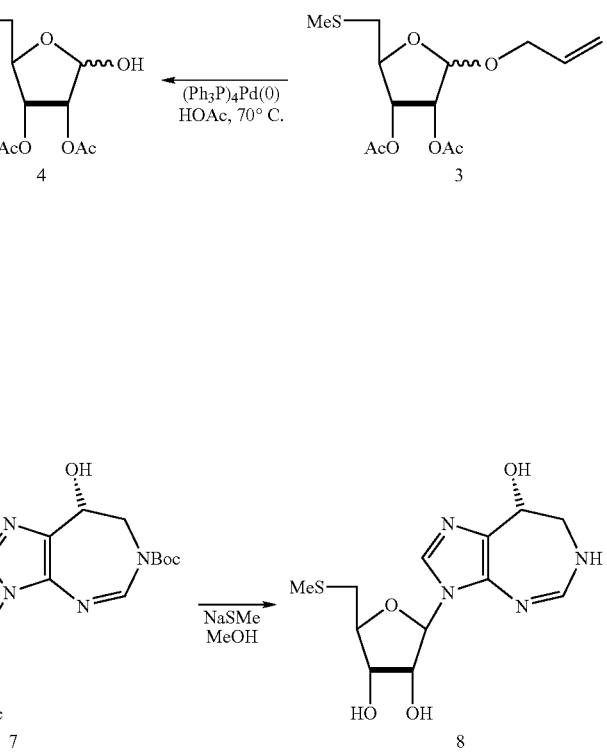

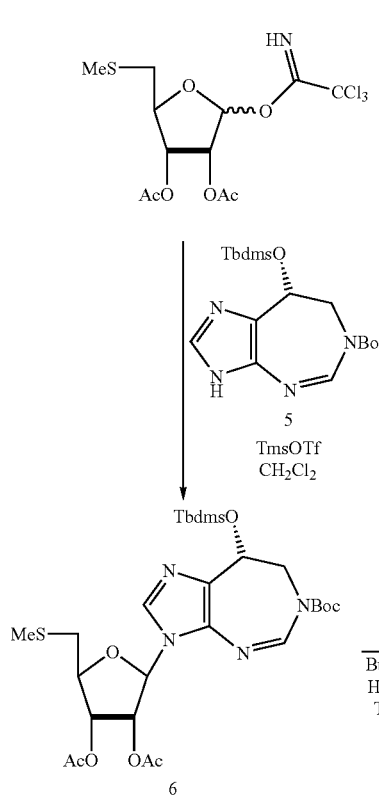

Example 1

Synthesis of 5'-methylthiocoformycin (8)

Example 1.1

Allyl α,β-D-ribofuranoside (1)

Acetyl chloride (4 mL) was added to a stirred suspension of D-ribose (15 g) in allyl alcohol (200 mL) whereupon the solid quickly dissolved. After 1 h pyridine (10 mL) was added and the solution was concentrated to dryness. Chromatography of the residue afforded the anomeric mixture of the title compounds 1 as a colourless syrup (18.6 g, 98%). $^1$H NMR (CD$_3$OD) δ 6.0-5.84 (2H, m), 5.4-4.9 (3H, m), 4.3-3.9 (5H, m), 3.8-3.5 (2H, m); $^{13}$C NMR (peaks of the major anomer) δ 136.1, 117.6, 108.3, 85.3, 76.7, 73.2, 69.7, 65.5.

Example 1.2

Allyl 5-O-p-toluenesulfonyl-α,β-D-ribofuranoside (2)

A solution of allyl α,β-D-ribofuranoside 1 (18.6 g) in dry pyridine (100 mL) was cooled in an ice bath and p toluenesulfonyl chloride (22.4 g, 1.2 eq) was added portion-wise keeping the reaction temperature <5° C. The resulting solution was allowed to warm slowly to RT overnight and then was concentrated to dryness. 1,4-Dioxane (100 mL) was added to the residue and it was again concentrated to dryness. Chromatography of the residue afforded an anomeric mixture of the title compounds 3 as a syrup (17.6 g, 52%). $^1$H NMR (CDCl$_3$) δ 7.80 (2H, d, J=8.3 Hz), 7.34 (2H, d, J=8.0 Hz), 5.85-5.72 (1H, m), 5.25-5.11 (2H, m), 4.94 (1H, s), 4.27-3.98 (6H, m), 3.87-3.80 (1H, m), 2.44 (3H, s); $^{13}$C NMR δ 145.5, 134.1, 133.0, 130.3, 128.4, 117.9, 106.6, 80.8, 75.2, 72.3, 71.0, 68.6, 22.0.

Example 1.3

Allyl 2,3-di-O-acetyl-5-methylthio-α,β-D-ribofuranoside (3)

Sodium thiomethoxide (4.1 g) was added to a solution of allyl 5-O-p-toluenesulfonyl-α,β-D-ribofuranoside (2) (6.7 g) in N,N-dimethylformamide (30 mL). The resulting solution became hot and after 1 h pyridine (50 mL) and acetic anhydride (50 mL) were added and the mixture was stirred overnight at RT. Toluene (100 mL) was added and the whole was washed with water, 2M aq HCl and saturated aq NaHCO$_3$. Normal processing afforded an anomeric mixture of the title product 3 that was separated by chromatography (4.16 g and 0.73 g, total 82%). For the less polar major component $^1$H NMR (CDCl$_3$) δ 5.94-5.83 (1H, m), 5.34-5.26 (4H, m), 5.04 (1H, s), 4.30-4.19 (2H, m), 4.04-3.98 (1H, m), 2.77-2.75 (2H, m), 2.18, 2.10, 2.06 (3H each, s); $^{13}$C NMR δ 170.1, 170.0, 133.9, 117.9, 104.7, 80.8, 75.5, 74.8, 68.9, 38.8, 20.9, 16.6. For the minor more polar isomer $^1$H NMR (CDCl$_3$) δ 5.95-5.84 (1H, m), 5.34-5.02 (5H, m), 4.35-4.21 (2H, m), 4.12-4.04 (1H, m), 2.87 (1H, dd, J=4.6 and 14.0 Hz), 2.78 (1H, dd, J=5.5 and 14.0 Hz), 2.18, 2.12, 2.11 (3H each, s); $^{13}$C NMR δ 170.8, 170.2, 134.4, 117.5, 99.8, 81.6, 72.4, 71.3, 68.9, 37.1, 21.1, 20.9, 17.4.

Example 1.4

2,3-Di-O-acetyl-5-S-methyl-α,β-D-ribofuranose (4)

Tetrakis(triphenyl-phosphine)palladium(0)-(5.3 g) was added to a solution of allyl 2,3-di-O-acetyl-5-methylthio-α, β-D-ribofuranoside (3) (3.48 g) in acetic acid (70 mL) and the solution was stirred under argon at 70° C. After 1.5 h further palladium catalyst (1.0 g) was added and then after a further 1 h the solution was concentrated to dryness. Chromatography of the residue gave the title compound 4 as a syrup (1.9 g, 63%) as a mixture of anomers; $^{13}$C NMR (CDCl$_3$) δ 170.3, 170.2, 170.1, (100.4 and 95.7), (81.6 and 80.4), (76.2 and 73.9), (73.0 and 71.5), (38.5 and 37.2), 21.1, 20.9, 20.8, (17.3 and 17.0).

Example 1.5

(8R)-6-(tert-Butoxycarbonyl)-8-[(tert-butyldimethylsilyl)oxy]-3-(2',3'-di-O-acetyl-5'-methylthio-β-D-ribofuranosyl)-3,6,7,8-tetrahydroimidazo[4,5-d][1,3]diazepine (6)

A solution of 2,3-di-O-acetyl-5-methylthio-α,β-D-ribofuranose (4) (0.60 g) in dichloromethane (5 mL) was treated with trichloroacetonitrile (1.5 mL) and then 1,8-diazabicyclo[5.4.0]undec-7-ene (4 drops). After 0.5 h the solution was diluted with hexanes and subjected directly to flash chromatography, eluting with 25% ethyl acetate in hexanes containing 0.5% triethylamine affording a syrup (0.67 g) of the trichloroacetimidate glycosyl donor. To a solution of this material and (8R)-6-(tert-butoxycarbonyl)-8-[(tert-butyldimethylsilyl)oxy]-3,6,7,8-tetrahydroimidazo[4,5-d][1,3]diazepine (5) (0.12 g) (prepared as described in T. V. Truong and H. Rapoport *J. Org. Chem.* 1993, 58, 6090-6096) in dichloromethane (8 mL) at 0° C. under argon was added trimethylsilyl triflate (0.155 mL) and then the solution was allowed to warm to RT. The solution was then washed with saturated aq NaHCO$_3$ and processed normally. Chromatography of the crude residue (EtOAc/CHCl$_3$/Hexanes 1:2:4 plus 1% Et$_3$N) afforded a syrup (0.162 g, 80%). $^1$H NMR (CDCl$_3$) δ 7.88 (1H, s), 7.60 (1H, s), 6.03 (1H, d, J=5.0 Hz), 5.80 (1H, t, J=5.5 Hz), 5.50 (1H, t, J=5.5 Hz), 5.13 (1H, d, J=4.4 Hz), 4.48 (1H, dd, J=13.5, 4.6 Hz), 4.34 (1H, dd, J=10.6, 5.3 Hz), 3.13 (1H, d, J=13.5 Hz), 2.87 (2H, m), 2.14, 2.10, 2.08 (3H each, s), 1.54 (9H, s), 0.88 (9H, s), 0.19 (3H, s), 0.05 (3H, s); $^{13}$C NMR δ 169.9, 169.7, 152.8, 142.8, 135.0, 133.2, 86.4, 83.9, 82.0, 73.9, 72.8, 67.6, 47.2, 36.9, 28.5, 26.2, 20.9, 20.8, 18.7, 17.4, 4.2, −4.6. HRMS (MH$^+$ calcd for C$_{27}$H$_{45}$N$_4$O$_8$SSi: 613.2727. found: 613.2724

Example 1.6

(8R)-6-(tert-Butoxycarbonyl)-8-hydroxy-3-(2',3'-di-O-acetyl-5'-S-methyl-O-D-ribofuranosyl)-3,6,7,8-tetrahydroimidazo[4,5-d][1,3]diazepine (7)

Acetic acid (0.05 mL) and then tetrabutylammonium fluoride (1M in THF, 2.0 mL) was added to a solution of (8R)-6-(tert-butoxycarbonyl)-8-[(tert-butyldimethylsilyl)oxy]-3-(2',3'-di-O-acetyl-5'-methylthio-β-D-ribofuranosyl)-3,6,7,8-tetrahydroimidazo[4,5-d][1,3]diazepine (6) (0.25 g) in THF (2.0 mL). After it was allowed to stand at RT for 48 h the solution was evaporated to dryness. Chromatography of the residue (EtOAc) afforded the title compound 7 as a colourless foam (0.143 g, 70%). $^1$H NMR (CDCl$_3$) δ 7.86 (1H, s), 7.68 (1H, s), 6.06 (1H, d, J=5.2 Hz), 5.77 (1H, t, J=5.4 Hz), 5.48 (1H, t, J=5.4 Hz), 4.98 (1H, brs), 4.35 (1H, dd, J=10.4, 5.2 Hz), 3.94-3.75 (2H, m), 2.94-2.82 (2H, m), 2.15, 2.11, 2.09 (3H each, s), 1.55 (9H, s); $^{13}$C NMR δ 170.0, 169.7, 152.7, 143.3, 133.6, 86.4, 84.3, 82.1, 73.9, 72.7, 65.7, 46.7, 36.9, 28.5, 20.9, 20.8, 17.4. HRMS (MH$^+$ calcd for C$_{21}$H$_{31}$N$_4$O$_8$S: 499.1863. found: 499.1867.

Example 1.7

5'-Methylthiocoformycin (8R)-8-Hydroxy-3-5'-methylthio-β-D-ribofuranosyl)-3,6,7,8-tetrahydroimidazo[4,5-d][1,3]diazepine (8)

Sodium thiomethoxide (0.15 g) was added to a solution of (8R)-6-(tert-butoxycarbonyl)-8-hydroxy-3-(2',3'-di-O-acetyl-5'-methylthio-β-D-ribofuranosyl)-3,6,7,8-tetrahydroimidazo[4,5-d][1,3]diazepine (7) (0.029 g) in methanol (2 mL) and the solution was stirred at RT for 4 h, then concentrated to dryness. Chromatography of the residue (7M NH$_3$ in MeOH/CH$_2$Cl$_2$ 3:7) gave 5'methylthiocoformycin (8) as a white solid (0.014 g, 76%). $^1$H NMR (CD$_3$OD) δ 8.00 (1H, s), 7.16 (1H, s), 5.93 (1H, d, J=4.3 Hz), 5.01 (1H, dd, J=4.5, 2.2 Hz), 4.43 (1H, t, J=4.5 Hz), 4.23-4.16 (2H, m), 3.46-3.30 (2H, m), 2.94-2.79 (2H, m), 2.15 (3H, s); $^{13}$C NMR δ 150.9, 137.5, 131.5, 128.4, 90.2, 85.3, 76.4, 74.1, 67.7, 37.9, 17.1. HRMS (MH$^+$ calcd for C$_{12}$H$_{19}$N$_4$O$_4$S: 315.1127. found: 315.1124.

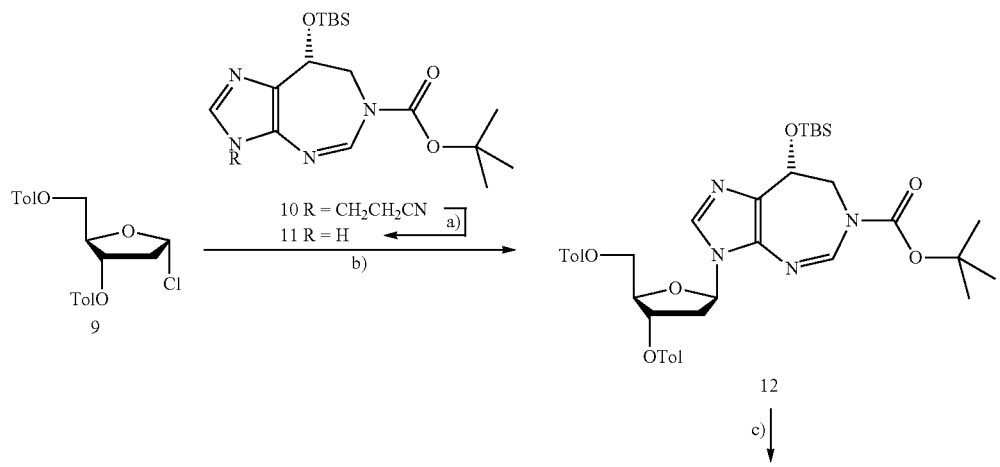

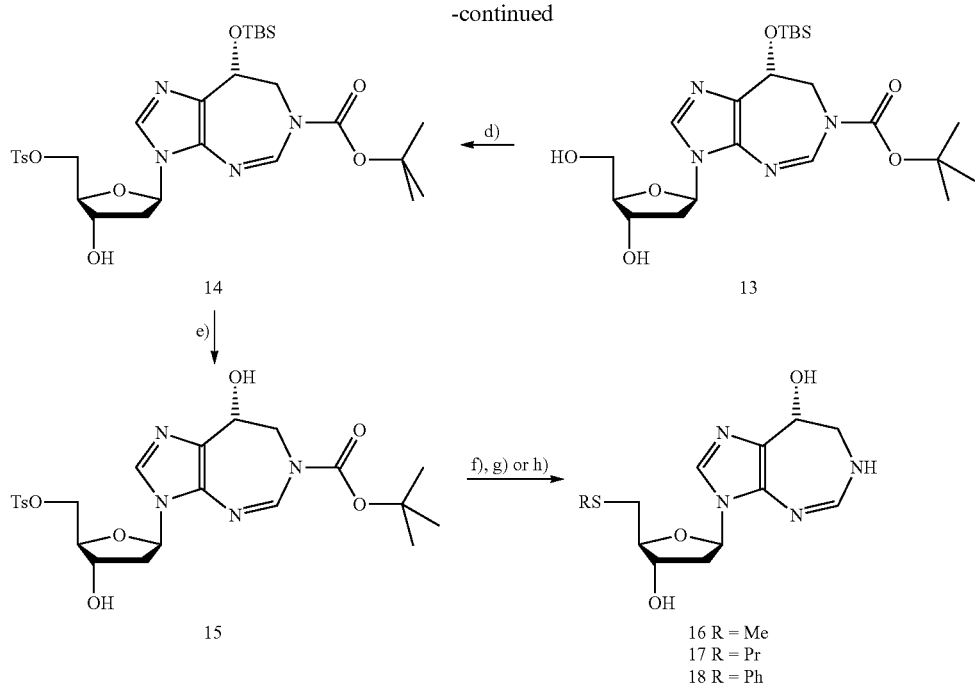

a) KO'Bu, THF, 77%; b) NaH, CH₃CN, 85%; c) NH₃, MeOH, 71%; d) TsCl, pyridine, 60%; e) NH₄F, MeOH, reflux, 58%; f) NaSMe, MeOH, 73%; g) PrSH, NaOMe, MeOH, 68%; h) (1) PhSH, NaOMe, MeOH, (2) NaSMe, 90%.

Example 2

Synthesis of 2'-deoxy-5'-methylthiocoformycin (16)

Example 2.1

(8R)-6-tert-Butoxycarbonyl)-8-(tert-butyldimethylsilyloxy)-3-(2'-deoxy-3',5'-di-O-tolyl-β,D-erythro-pentofuranosyl)-3,6,7,8-tetrahydroimidazo[4,5-d][1,3]diazepine (12)

(8R)-6-(tert-Butoxycarbonyl)-8-(tert-butyldimethylsilyloxy)-3-(2'-cyanoethyl)-3,6,7,8-tetrahydroimidazo[4,5-d][1,3]diazepine 10 (0.76 g, 1.81 mmol) was dissolved in dry THF (15 mL) and potassium tert-butoxide (1.0 M in THF, 3.6 mL) was added at RT. The mixture turned brown immediately and was quenched by addition of glacial acetic acid (206 µL, 3.6 mmol) and coevaporated with toluene (30 mL). The residue was suspended in chloroform/ethyl acetate (5 mL, 1:2 v/v) by ultrasonification and applied on a chromatography column (50 g silica, chloroform/ethyl acetate=1:2 v/v, then ethyl acetate), which gave (8R)-6-(tert-butoxycarbonyl)-8-(tert-butyldimethylsilyloxy)-3,6,7,8-tetrahydro-imidazo[4,5-d][1,3]diazepine 11 as an amorph yellow solid (0.51 g, 1.39 mmol, 77%). 11 was dissolved in dry acetonitrile (10 mL) and evaporated in vacuo, flushed with Argon and redissolved again in dry acetonitrile (15 mL). Addition of sodium hydride (60% in mineral oil, 72 mg) gave a visible gas formation. After 30 min 2-deoxy-3,5-di-O-(p-toluoyl)-D-erythro-pentofuranosyl chloride 9 (made according to Chem. Ber. 1960, 93, 2777-2781) (0.70 g, 1.81 mmol) was added to the reaction mixture, a thick heterogeneous slurry was formed. After further 40 min the reaction mixture was filtered through flux calcined diatomaceous earth and rinsed thoroughly with ethyl acetate. The filtrate was evaporated to dryness in vacuo. Purification of the residue by chromatography (60 g silica, petroleum ether/ethyl acetate=2:1 v/v) gave 12 as yellowish oil (0.85 g, 1.18 mmol, 85% calcd. from 11). $R_f$=0.31 (petrol ether/EtOAc=3:2 v/v), $[α]_D^{20}$=−17.4 (c 11.8, chloroform), $^1$H-NMR: (CDCl₃) δ 0.05 (s, 3H, SiMe), 0.19 (s, 3H, SiMe), 0.88 (s, 9H, Si'Bu), 1.54 (s, 9H, O'Bu), 2.40 (s, 3H, ArMe), 2.43 (s, 3H, ArMe), 2.70 (ddd, J=2.2, 5.9, 14.2 Hz, 1H, H-2'), 2.84 (ddd, J=6.4, 8.4, 14.2 Hz, 1H, H-2'), 3.08 (br d, J=13.6 Hz, 1H, H-7), 4.50 (dd, J=4.4, 13.6 Hz, 1H, H-7), 4.55-4.60 (m, 1H, H-4'), 4.61-4.65 (m, 2H, H-5'), 5.13 (br d, J=4.4 Hz, H-8), 5.70 (ddd, J=2.2, 2.3, 6.0 Hz, 1H, H-3'), 6.42 (dd, J=5.9, 8.4 Hz, 1H, H-1'), 7.19-7.30 (m, 4H, Ar), 7.57 (s, 1H, H-2), 7.85-7.99 (m, 5H, 4×Ar and H-5), $^{13}$C-NMR: (CDCl₃) δ −4.6 (SiMe), −4.2 (SiMe), 18.6 (SiC(CH₃)₃), 22.0 (ArCH₃), 26.2 (SiC(CH₃)₃), 28.5 (OC(CH₃)₃), 38.9 (C-2'), 47.2 (C-7), 64.6 (C-5'), 67.6 (C-8), 75.6 (C-3'), 82.7 (C-4'), 83.7 (OC(CH₃)₃), 84.4 (C-1'), 127.0, 127.2, 129.6, 130.1, 130.2, 132.3 (C-2), 133.1, 134.8, 142.7 (C-5), 144.4, 144.7, 152.8, 166.3, 166.6, HRMS: (MH⁺) calcd. for $C_{38}H_{51}N_4O_8Si^+$: 719.3476. found: 719.3492.

Example 2.2

(8R)-6-tert-Butoxycarbonyl)-8-(tert-butyldimethylsilyloxy)-3-(2'-deoxy-β,D-erythro-pentofuranosyl)-3,6,7,8-tetrahydroimidazo[4,5-a][1,3]diazepine (13)

In a rubber sealed round bottom flask 12 (0.79 g, 1.10 mmol) was treated with ammonia (7M in methanol, 75 mL) at RT. After 17 h the mixture was evaporated in vacuo, the residue was transferred into an ace pressure tube, fresh ammonia (7 M in methanol, 50 mL) was added, the tube was sealed and warmed to 45° C. for another 4 h. After evaporation in vacuo the residue was purified by chromatography (41 g silica, chloroform/methanol=15:1 v/v) which gave 13 as colourless oil (375 mg, 71%). $R_f$=0.34 (chloroform/methanol=10:1 v/v), $[α]_D^{20}$=+10.0 (c 5.23, chloroform), $^1$H-NMR:

(CDCl$_3$) δ 0.06 (s, 3H, SiMe), 0.19 (s, 3H, SiMe), 0.88 (s, 9H, Si$^t$Bu), 1.53 (s, 9H, O$^t$Bu), 2.25 (ddd, J=1.1, 5.9, 14 Hz, 1H, H-2'), 2.94 (ddd, J=5.3, 8.7, 14 Hz, 1H, H-2'), 3.08 (br d, J=13.6 Hz, 1H, H-7), 3.74 (dd, J=1.3, 12.2 Hz, 1H, H-5'), 3.89 (dd, J=1.8, 12.2 Hz, 1H, H-5'), 4.10-4.15 (m, 1H, H-4'), 4.54 (dd, J=4.7, 13.6 Hz, 1H, H-7), 4.65-4.71 (m, 1H, H-3'), 5.14 (d, J=4.7 Hz, 1H, H-8), 6.20 (dd, J=5.9, 8.7 Hz, 1H, H-1'), 7.49 (s, 1H, H-2), 7.85 (s, 1H, H-5), $^{13}$C-NMR: (CDCl$_3$) δ −4.6 (SiMe), 4.3 (SiMe), 18.7 (SiC(CH$_3$)$_3$), 26.2 (SiC(CH$_3$)$_3$), 28.5 (OC(CH$_3$)$_3$), 41.6 (C-2'), 47.0 (C-7), 63.5 (C-5'), 67.6 (C-8), 73.3 (C-3'), 84.3 (OC(CH$_3$)$_3$), 87.3 (C-1'), 88.7 (C-4'), 132.7, 134.9 (C-2), 136.2, 143.3 (C-5), 152.6, HRMS: (MH$^+$) calcd. for C$_{22}$H$_{39}$N$_4$O$_6$Si$^+$: 483.2639. found: 483.2643.

Example 2.3

(8R)-6-tert-Butoxycarbonyl)-8-(tert-butyldimethylsilyloxy)-3-(2'-deoxy-5'-O-p-toluenesulfonyl-β,D-erythro-pentofuranosyl)-3,6,7,8-tetrahydroimidazo[4,5-c][1,3]diazepine (14)

13 (0.375 g, 0.777 mmol) was dissolved in dry pyridine (7 mL, 87 mmol) and p-toluenesulfonyl chloride (0.222 g, 1.17 mmol) was added at 0° C. After 20 min the mixture was warmed to RT and stirred overnight. The reaction mixture was diluted with chloroform (30 mL) and consecutively washed with water (40 mL), citric acid (5% w/w, 3×50 mL) and saturated NaHCO$_3$ (60 mL), dried (MgSO$_4$) and evaporated in vacuo. The residue was purified by chromatography (46 g silica, chloroform/methanol=20:1 v/v) which gave the title compound as a glass (313 mg, 63%). R$_f$=0.39 (chloroform/methanol=10:1 v/v), [α]$_D^{20}$=+25.8 (c 3.62, CHCl$_3$), $^1$H-NMR: (CDCl$_3$) δ 0.07 (s, 3H), 0.20 (s, 3H), 0.88 (s, 9H), 1.54 (s, 9H), 2.43 (m, 4H), 2.34-2.46 (m, 4H), 2.55-2.66 (m, 2H, 1H D$_2$O exchangeable), 3.07 (br d, J=13.5 Hz, 1H), 4.06-4.16 (m, 2H), 4.20-4.29 (m, 1H), 4.48 (dd, J=4.5, 13.5 Hz, 1H), 4.60-4.70 (m, 1H), 5.12 (br d, J=4.5 Hz, 1H), 6.30 (t, J=6.7 Hz, 1H), 7.28-7.34 (m, 2H), 7.48 (s, 1H), 7.70-7.75 (m, 2H), 7.83 (s, 1H), $^{13}$C-NMR: (CDCl$_3$) δ −4.6, −4.1, 18.7, 22.0, 26.2, 28.5, 40.6, 47.2, 67.6, 69.1, 72.2, 83.8, 83.9, 128.4, 130.4, 132.4, 132.6, 133.0, 134.6, 142.6, 145.6, 152.8, HRMS: (MH$^+$) calcd. for C$_{29}$H$_{45}$N$_4$O$_8$SSi$^+$: 637.2727. found: 637.2753.

Example 2.4

(8R)-6-(tert-Butoxycarbonyl)-3-2'-deoxy-5'-O-p-toluenesulfonyl-β,D-erythro-pentofuranosyl)-8-hydroxy-3,6,7,8-tetrahydroimidazo[4,5-a][1,3]diazepine (15)

14 (0.31 g, 0.49 mmol) was dissolved in dry methanol (12 mL) and ammonium fluoride (0.54 g, 14.6 mmol) was added and the mixture was heated to reflux for 6.5 h. After cooling to RT stirring was continued overnight. The next morning the mixture put to reflux again for further 6 h. The reaction mixture was evaporated in vacuo and the residue was purified by chromatography (27 g silica, chloroform/methanol=10:1 v/v) which gave 15 as a hard foam (147 mg, 58%). R$_f$=0.23 (chloroform/methanol=10:1 v/v), [α]$_D^{20}$=+30.3 (c 2.15, chloroform), $^1$H-NMR: (CDCl$_3$) δ 1.53 (s, 9H), 2.37-2.64 (m, 6H), 3.59 (br d, J=13.5 Hz, 1H), 4.03 (dd, J=5.9, 13.5 Hz, 1H), 4.08-4.17 (m, 3H), 4.18-4.26 (m, 1H), 4.58-4.67 (m, 1H), 5.01 (d, J=2.0, 5.9 Hz, 1H), 6.31 (t, J=6.6 Hz, 1H), 7.27-7.32 (m, 2H), 7.59 (s, 1H), 7.67-7.73 (m, 2H), 7.80 (s, 1H), $^{13}$C-NMR: (CDCl$_3$) δ 22.0, 28.4, 40.8, 46.8, 65.8, 69.4, 71.6, 84.0, 84.2, 128.3, 130.4, 132.3, 132.6, 133.0, 134.2, 142.9, 145.6, 152.9, HRMS: (MH$^+$) calcd. for C$_{23}$H$_{31}$N$_4$O$_8$S$^+$: 523.1863. found: 523.1848.

Example 2.5

(8R)-3-(2'-deoxy-5'-methylthio-β,D-erythro-pentofuranosyl)-8-hydroxy-3,6,7,8-tetrahydroimidazo[4,5-d][1,3]diazepine (16)

Under argon 15 (35 mg, 0.067 mmol) was dissolved in dry methanol (3 mL) and treated with sodium thiomethoxide (95% w/w, 0.30 g) at RT. After 2 h the reaction mixture was evaporated in vacuo. Purification of the residue by chromatography (12 g silica, chloroform/methanolic ammonia (7M)= 5:1 v/v, 120 mL, 4:1 v/v 100 mL) gave 16 as a white solid (14.5 mg, 73%). R$_f$=0.35 (chloroform/methanolic ammonia (7M)=4:1 v/v), [α]$_D^{20}$=+89 (c 0.41, methanol), $^1$H-NMR: (D$_2$O) δ 2.09 (s, 3H, SMe), 2.48 (ddd, J=4.1, 6.4, 14.1 Hz, 1H, H-2'), 2.68 (ddd, J=6.7, 7.2, 14.1 Hz, 1H, H-2'), 2.74 (dd, J=6.6, 14.1 Hz, 1H, H-5'), 2.82 (dd, J=5.7, 14.1 Hz, 1H, H-5'), 3.34 (br d, J=13.5 Hz, 1H, H-7), 3.49 (dd, J=4.4, 13.5 Hz, 1H, H-7), 4.16 (ddd, J=3.5, 6.0, 6.2 Hz, 1H, H-4'), 4.52 (m, 1H, H-3'), 5.12 (br d, J=3.5 Hz, 1H, H-8), 6.25 (t, J=6.8 Hz, 1H, H-1'), 7.20 (s, 1H), 7.75 (s, 1H), $^{13}$C-NMR: (D$_2$O) δ 15.8 (SMe), 36.7 (C-5'), 39.1 (C-2'), 47.7 (C-7), 67.2 (C-8), 73.8 (C-3'), 83.2 (C-1'), 85.8 (C-4'), 128.4, 131.4 (C-2), 135.9, 151.0 (C-5), HRMS: (MH$^+$) calcd. for C$_{12}$H$_{19}$N$_4$O$_3$S$^+$: 299.1178. found: 299.1187, Anal. calcd. for C$_{12}$H$_{18}$N$_4$O$_3$S.1.4H$_2$O: C, 44.54; H, 6.48; N, 17.31; S, 9.91. found: C, 44.42; H, 6.13; N, 17.19; S, 9.69.

Example 3

Synthesis of 2'-deoxy-5'-propylthiocoformycin (17)

Example 3.1

(8R)-3-(2'-deoxy-5'-propylthio-β,D-erythro-pentofuranosyl)-8-hydroxy-3,6,7,8-tetrahydroimidazo[4,5-d][1,3]diazepine (17)

1-Propanethiol (0.42 mL, 4.64 mmol) was diluted in dry methanol (3 mL) and sodium methoxide (30% w/w in methanol, 0.72 mL) was added. After 5 min at RT 15 (40 mg, 0.077 mmol) was added and the mixture was stirred overnight at RT. The next day the solution was evaporated in vacuo and purified by chromatography (15 g silica, chloroform/methanolic ammonia (7M)=5:1 v/v) which gave product as white soapy material (17 mg, 68%). R$_f$=0.31 (chloroform/methanolic ammonia (7M)=4:1 v/v). [α]$_D^{20}$=+76 (c 0.85, methanol), $^1$H-NMR: (CD$_3$OD) δ 0.97 (t, J=7.3 Hz, 3H), 1.60 (sext, J=7.3 Hz, 2H), 2.35 (ddd, J=3.9, 6.3, 13.5 Hz, 1H, H-2'), 2.47 (dd, J=6.9, 13.5 Hz, 1H, H-2'), 2.55 (t, J=7.3 Hz, 2H), 2.76 (dd, J=5.9, 13.8 Hz, 1H, H-5'), 2.81 (dd, J=5.9, 13.8 Hz, 1H, H-5'), 3.27-3.35 (m, 1H, H-7), 3.39 (dd, J=4.4, 13.1 Hz, 1H, H-7), 4.02 (ddd, J=3.5, 5.9, 5.9 Hz, 1H, H-4'), 4.35-4.43 (m, 1H, H-3'), 4.98-5.05 (m, 1H, H-8), 6.27 (t, J=6.8 Hz, 1H, H-1'), 7.08 (s, 1H), 7.66 (s, 1H), $^{13}$C-NMR: (CD$_3$OD) δ 13.7, 24.0, 35.7, 35.9, 41.4 (C-2'), 49.1 (C-7), 68.4 (C-8), 74.5 (C-3'), 84.4 (C-1'), 87.6 (C-4'), 130.3 (C-2), 131.4, 136.8, 149.8 (C-5), HRMS: (MH$^+$) calcd. for C$_{14}$H$_{23}$N$_4$O$_3$S$^+$: 327.1491. found: 327.1487, Anal. calcd. for C$_{14}$H$_{22}$N$_4$O$_3$S: C, 51.51; H, 6.79; N, 17.16. found: C, 51.49; H, 6.77; N, 16.94.

Example 4

Synthesis of 2'-deoxy-5'-phenylthiocoformycin (18)

Example 4.1

(8R)-3-(2'-deoxy-5'-phenylthio-β,D-erythro-pento-furanosyl)-8-hydroxy-3,6,7,8-tetrahydroimidazo[4,5-d][1,3]diazepine (18)

Under argon sodium methoxide (30% w/w in methanol, 0.72 mL) was added to a solution of thiophenol (0.47 mL, 4.6 mmol) in dry methanol (3 mL). After 5 min 15 (39 mg, 0.075 mmol) was added, and the solution was stirred at RT for 24 h. Sodium thiomethoxide (95%, 0.32 g) was added to the mixture and stirred for further 3 h 20 min. The reaction mixture was concentrated in vacuo, redissolved in chloroform/methanol (4:1 v/v), silica (1 g) was added and again concentrated to dryness in vacuo and applied to a column (14 g silica, chloroform/methanol=10:1 v/v 200 mL washed off excess thiophenol, then 4:1 v/v 100 mL eluted the product) which gave compound 18 as an oil (24 mg, 90%). $R_f$=0.21 (chloroform/methanol=4:1 v/v), $[\alpha]_D^{20}$=+83 (c 0.49, methanol), $^1$H-NMR: (CD$_3$OD) δ 2.35 (ddd, J=3.4, 6.2, 13.6 Hz, 1H, H-2'), 2.51 (ddd, J=6.2, 7.4, 13.6 Hz, 1H, H-2'), 3.19 (dd, J=6.0, 13.8 Hz, 1H, H-5'), 3.24 (dd, J=6.1, 13.8 Hz, 1H, H-5'), 3.27-3.34 (m, 1H, H-7), 3.39 (dd, J=4.4, 13.2 Hz, 1H, H-7), 4.05 (ddd, J=3.1, 6.0, 6.1 Hz, 1H, H-4'), 4.41 (ddd, J=3.0, 3.2, 6.2 Hz, 1H, H-3'), 5.01 (dd, J=1.4, 4.4 Hz, 1H, H-8), 6.26 (dd, J=6.2, 7.4 Hz, 1H, H-1'), 7.07 (s, 1H, H-5), 7.14-7.22 (m, 1H), 7.23-7.32 (m, 2H), 7.36-7.43 (m, 2H), 7.59 (s, 1H, H-2). $^{13}$C-NMR: (CD$_3$OD) δ 37.7 (C-5'), 41.3 (C-2'), 49.1 (C-7), 68.4 (C-8), 74.6 (C-3'), 84.7 (C-1'), 86.6 (C-4'), 127.3, 130.1, 130.4, 130.6, 131.5 (C-2), 136.8, 137.5, 149.8 (C-5), HRMS: (MH$^+$) calcd. for C$_{17}$H$_{21}$N$_4$O$_3$S$^+$: 361.1334. found: 361.1324, Anal. calcd. for C$_{17}$H$_{20}$N$_4$O$_3$S.1.7H$_2$O: C, 52.21; H, 6.03; N, 14.33. found: C, 52.01; H, 5.75; N, 14.50.

Example 5

Enzyme Inhibition Studies

Adenosine deaminase activity was determined by monitoring the conversion of adenosine to inosine via the change in absorbance at 267 nm in assay mixtures containing 20 mM potassium phosphate, pH 7.0, 100 μM adenosine and 1 μM EDTA at 30° C. (V. L. Schramm, D. C. Baker, *Biochemistry*, 1985, 24, 641-646). Inhibitor concentrations ranging from 10 μM to 2 nM were used for determination of the inhibition constants and an enzyme concentration of 1 nM. The Ki values were determined by fitting the initial rate and inhibitor concentrations to the following expression of competitive inhibition:

$$(V'_o/V_o) = (K_M + [S])/(K_M + [S] + (K_M[I]/K_i))$$

where V'$_o$ is the initial rate in the presence of inhibitor, and V$_o$ is the initial rate in the absence of inhibitor, [I] is the inhibitor concentration, and [S] is the substrate concentration. This expression is valid only under the condition where the inhibitor concentration is 10 times greater than the enzyme concentration. In conditions where inhibitor concentration does not exceed ten times the enzyme concentration the effective inhibitor concentration was obtained by the expression:

$$I' = I - (1 - V'_o/V_o)E_t$$

where I' is the effective inhibitor concentration, V'$_o$ and V$_o$ are the initial rate in the presence and absence of inhibitor, and E$_t$ is the total enzyme concentration. In cases where slow onset inhibition was observed, where the inhibitor reached a tighter binding thermodynamic equilibrium with the enzyme, the equilibrium dissociation constant ($K_i^*$) was obtained by fitting the rates to the following equation for competitive inhibition:

$$(V'_o/V_o) = (K_M + [S])/(K_M + [S] + (K_M[I]/K_i^*))$$

with [I] concentrations being corrected as above (V. Singh, G. B. Evans, D. H. Lenz, J. M Mason, K. Clinch, S. Mee, G. F. Painter, P. C. Tyler, R. H. Furneaux, J. E. Lee, P. L. Howell, V. L. Schramm *J. Biol. Chem.*, 2005, 280, 18265-18273). The $K_M$ values for the enzymes are 16±2 μM for the bovine enzyme (V. L. Schramm, D. C. Baker, *Biochemistry*, 1985, 24, 641-646), 29±3 μM for the malarial enzyme (L.-M. Ting, et al., *J. Biol. Chem.*, 2005, 280, 9547-9554) and 22±2 μM for the human enzyme (the human enzyme sample received from Sigma was characterized to have a $k_{cat}$ of 36±1 sec$^{-1}$ and a $K_M$ of 22±2 μM).

The results of studies on the inhibition of human, bovine and *P. falciparum* ADA (i.e. HsADA, BtADA and PfADA, respectively) are detailed in Table 1.

TABLE 1

Inhibition values of transition state analogue inhibitors of adenosine deaminases

| Compound | BtADA | | HsADA | | PfADA | |
| --- | --- | --- | --- | --- | --- | --- |
| | $K_i$ (nM) | $K_i^a$ (nM) | $K_i$ (nM) | $K_i^a$ (nM) | $K_i$ (nM) | $K_i^a$ (nM) |
| Coformycin | 1.1 ± 0.4 | 0.06 ± 0.01 | 13.9 ± 3.4 | 0.11 ± 0.02 | 0.68 ± 0.07 | 0.08 ± 0.02 |
| 5'-MeS-Coformycin (8) | >10,000$^a$ | ND | >10,000 | ND | 2.66 ± 0.13 | 0.43 ± 0.12 |
| 2'-deoxycoformycin | 0.39 ± 0.12 | 0.027 ± 0.004 | 0.5 ± 0.1 | 0.026 ± 0.005 | 8.2 ± 2.9 | 0.038 ± 0.009 |
| 5'-MeS-2'-deoxycoformycin (16) | >10,000 | ND | >10,000 | ND | 2.3 ± 0.8 | 0.73 ± 0.22 |
| 5'-PrS-2'-deoxycoformycin (17) | >10,000 | ND | >10,000 | ND | 12 ± 1 | ND |
| 5'-PhS-2'-deoxycoformycin (18) | >10,000 | ND | >10,000 | ND | 61 ± 11 | ND |

$^a$$K_i$ values of >10,000 indicate that assays with 10 μM of the indicated inhibitor exhibited no inhibition under the conditions of the assay.

Example 3

*P. falciparum* Culture and 5'-methylcoformycin Kill Curves

Human erythrocytes were collected from local volunteers under protocol CCI 00-31 or CCI 99-240 of the Albert Einstein College of Medicine. Cultures of *P. falciparum* strain 3D7 were grown in RPMI supplemented with 0.5% Albumax II (Invitrogen) and were sorbitol-synchronized twice before initiation of the 72 hour assay in 96-well plates with a total volume of 200 μL at 1% hematocrit and 0.8% parasitemia (100% rings). Culture media for studies with coformycin and 5'-methylthiocoformycin contained no hypoxanthine supplementation. Drugs were dissolved in water and diluted with media prior to addition to cultures. Following incubation with coformycin or 5'-methylthiocoformycin with or without 5'-methylthioadenosine (Sigma) for 18 h, cultures were supplemented with 1 μCi of [$^3$H]ethanolamine (Amersham Biosciences, 25 Ci/mmol) per well. After 54 h, cell cultures were frozen and thawed to disrupt cells, and the mixtures were harvested on glass fiber filters. Filters were counted in a Winspectral 1414 scintillation counter. Experiments were done twice with six replicate wells for each experiment. Individual data points more than two standard deviations from the mean were discarded. For some experiments, parasitemias were counted on Giemsa-stained smears of cultures treated in parallel.

The results from a comparison of the ability of coformycin and 5'-methylthiocoformycin to prevent the growth of *P. falciparum* (as represented by uptake of tritiated ethanolamine) in red blood cells are shown in FIG. 1. The $IC_{50}$ value for coformycin was 3.5 nM, while that for 5'-methylthiocoformycin was 62 nM.

Visual inspection after 48 hours showed that red blood cells infected with *P. falciparum* to 1% parasitemia initially and with methylthioadenosine (100 μM) alone added to the culture media had 8% parasitemia and 97% of the parasites were in the ring form indicating proliferation. Equivalent red blood cells with methylthioadenosine (100 μM) and either coformycin (10 μM) or 5'-methylthiocoformycin (10 μM) separately, after 48 hours had only 1% parasitemia and 100% of the parasites were in the trophozoite form. This indicates that treatment with either coformycin or 5'-methylthiocoformycin was effective in killing the malaria parasite.

Although the invention has been described by way of example, it should be appreciated that variations or modifications may be made without departing from the scope of the invention. Furthermore, when known equivalents exist to specific features, such equivalents are incorporated as if specifically referred to in the specification.

Industrial Applicability

The compounds of the invention are considered to be potential therapeutic agents for the treatment or prevention of protozoan parasite infections, including malaria.

The invention claimed is:

1. A compound of formula (I):

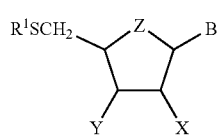

(I)

where
- $R^1$ is methyl, ethyl, propyl or phenyl;
- X is selected from hydrogen, hydroxyl and halogen;
- Y is selected from hydrogen and hydroxyl;
- Z is an oxygen atom; and
- B is the radical of formula (II):

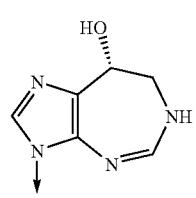

(II)

or a pharmaceutically acceptable salt thereof.

2. The compound as claimed in claim 1 which has the formula (IA):

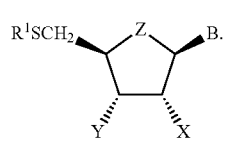

(IA)

3. The compound as claimed in claim 1 which has the formula (IB):

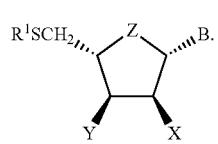

(IB)

4. The compound as claimed in claim 1 where $R^1$ is methyl.

5. The compound as claimed in claim 1 where X and Y are both hydroxyl.

6. The compound as claimed in claim 1 where X is hydroxyl and Y is hydrogen.

7. The compound as claimed in claim 1 where X is hydrogen and Y is hydroxyl.

8. The compound as claimed in claim 1 which is selected from:
   (i) 5'-methylthiocoformycin [(8R)-8-hydroxy-3-(5-methylthio-β-D-ribofuranosyl)-3,6,7,8-tetrahydroimidazo[4,5-d][1,3]diazepine];
   (ii) 2'-deoxy-5'-methylthiocoformycin [(8R)-8-hydroxy-3-(2-deoxy-5-methylthio-β-D-erythro-pentofuranosyl)-3,6,7,8-tetrahydroimidazo[4,5-d][1,3]diazepine];
   (iii) 3'-deoxy-5'-methylthiocoformycin [(8R)-8-hydroxy-3-(3-deoxy-5-methylthio-β-D-ribofuranosyl)-3,6,7,8-tetrahydroimidazo[4,5-d][1,3]diazepine];
   (iv) 2'-deoxy-5'-propylthiocoformycin [[(8R)-8-hydroxy-3-(5-propylthio-β-D-erythro-pentofuranosyl)-3,6,7,8-tetrahydroimidazo[4,5-d][1,3]diazepine]; and
   (v) 2'-deoxy-5'-phenylthiocoformycin [[(8R)-8-hydroxy-3-(5-phenylthio-β-D-erythro-pentofuranosyl)-3,6,7,8-tetrahydroimidazo[4,5-d][1,3]diazepine].

9. The compound as claimed in claim 1 which is 5'-methylthiocoformycin [(8R)-8-hydroxy-3-(5-methylthio-βD-ribofuranosyl)-3,6,7,8-tetrahydroimidazo[4,5-d][1,3]diazepine].

10. A pharmaceutical composition comprising a pharmaceutically effective amount of the compound of claim 1.

11. The pharmaceutical composition as claimed in claim 10 where the compound is selected from:
   (i) 5'-methylthiocoformycin [(8R)-8-hydroxy-3-(5-methylthio-β-D-ribofuranosyl)-3,6,7,8-tetrahydroimidazo[4,5-d][1,3]diazepine];
   (ii) 2'-deoxy-5'-methylthiocoformycin [(8R)-8-hydroxy-3-(2-deoxy-5-methylthio-β-D-erythro-pentofuranosyl)-3,6,7,8-tetrahydroimidazo[4,5-d][1,3]diazepine];
   (iii) 3'-deoxy-5'-methylthiocoformycin [(8R)-8-hydroxy-3-(3-deoxy-5-methylthio-β-D-ribofuranosyl)-3,6,7,8-tetrahydroimidazo[4,5-d][1,3]diazepine];
   (iv) 2'-deoxy-5'-propylthiocoformycin [[(8R)-8-hydroxy-3-(5-propylthio-β-D-erythro-pentofuranosyl)-3,6,7,8-tetrahydroimidazo[4,5-d][1,3]diazepine]; and
   (v) 2'-deoxy-5'-phenylthiocoformycin [[(8R)-8-hydroxy-3-(5-phenylthio-β-D-erythro-pentofuranosyl)-3,6,7,8-tetrahydroimidazo[4,5-d][1,3]diazepine].

12. The pharmaceutical composition of claim 10 comprising a pharmaceutically effective amount of 5'-methylthiocoformycin [(8R)-8-hydroxy-3-(5-methylthio-β-D-ribofuranosyl)-3,6,7,8-tetrahydroimidazo[4,5-d][1,3]diazepine].

13. A method of treating or preventing a protozoan parasite infection comprising administering a pharmaceutically effective amount of the compound of claim 1 to a patient requiring treatment.

14. The method as claimed in claim 13 where the infection is caused by a protozoan parasite of the genera *Giardia, Trichomonas, Leishmania, Trypanosoma, Crithidia, Herpetomonas, Leptomonas, Histomonas, Eimeria, Isopora, Neospora,* or *Plasmodium*.

15. The method as claimed in claim 13 where the infection is malaria.

16. The method as claimed in claim 13 where the infection is malaria and the compound is 5'-methylthiocoformycin [(8R)-8-hydroxy-3-(5-methylthio-β-D-ribofuranosyl)-3,6,7,8-tetrahydroimidazo[4,5-d][1,3]diazepine].

17. A process for preparing a compound of formula (I) as claimed in claim 1 comprising the following steps:
step (i) reacting a glycosyl donor compound of formula (III):

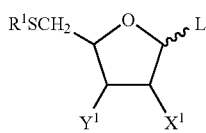
(III)

where
   L is a leaving group;
   X¹ is selected from hydrogen, halogen, acyloxy, and arylcarbonyloxy; and Y¹ is selected from hydrogen and acyloxy; or
   X¹ and Y¹ are oxygen atoms linked together by a protecting group; and
   R¹ is methyl, ethyl, propyl or phenyl;
with a compound of formula (IV) in the presence of a glycosyl donor activating reagent:

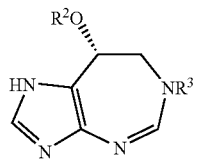
(IV)

where
   R² is a protecting group; and
   R³ is a protecting group; and
step (ii) removing the protecting groups to give hydroxyl or amine groups by any one or more of:
   (a) acid- and/or base-catalyzed hydrolysis;
   (b) acid- and/or base-catalyzed alcoholysis; and
   (c) catalytic hydrogenolysis.

18. A process for preparing a compound of formula (I) as claimed in claim 1 comprising the following steps:
step (i) selective sulfonylation of the primary hydroxyl group of a compound of formula (V):

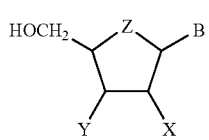
(V)

where
   X is selected from hydrogen, hydroxyl and halogen;
   Y is selected from hydrogen and hydroxyl;
   Z is an oxygen atom; and
   B is the radical of formula (VI)

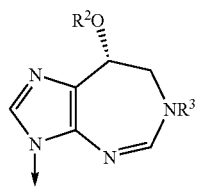
(VI)

where
   R² is a protecting group; and
   R³ is a protecting group;
   step (ii) reacting the product with a thiolate salt of formula R¹SM, where M is a metal cation and R¹ is methyl, ethyl, propyl or phenyl; and
   step (iii) removing any remaining protecting groups.

19. The process of claim 18, further comprising preparing the compound of formula (V) by:
reacting a glycosyl donor compound of formula (III):

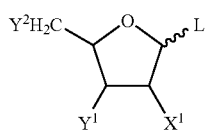
(III)

where
L is a leaving group;
X$^1$ is selected from hydrogen, halogen, acyloxy, and arylcarbonyloxy; and
Y$^1$ is selected from hydrogen and acyloxy; or
X$^1$ and Y$^1$ are oxygen atoms linked together by a protecting group; and
Y$^2$ is acyloxy;
with a compound of formula (IV) in the presence of a glycosyl donor activating reagent or a metal hydride such as sodium hydride

(IV)

where
R$^2$ is a protecting group; and
R$^3$ is a protecting group; and
removing the protecting groups on the sugar moiety to give hydroxyl groups by any one or more of:
(a) acid- and/or base-catalyzed hydrolysis;
(b) acid- and/or base-catalyzed alcoholysis; and
(c) catalytic hydrogenolysis.

* * * * *